(12) United States Patent
Troussel et al.

(10) Patent No.: US 6,355,039 B1
(45) Date of Patent: Mar. 12, 2002

(54) FLEXIBLE FASTENING DEVICE

(75) Inventors: Serge Troussel, Lasne (BE); Jean Moulin, Kayl (LU)

(73) Assignee: Bone & Joint Research S.A., Luxembourg (LU)

(*) Notice: Subject to any disclaimer, the term of this patent is extended or adjusted under 35 U.S.C. 154(b) by 6 days.

(21) Appl. No.: 09/645,854

(22) Filed: Aug. 24, 2000

(30) Foreign Application Priority Data

Sep. 3, 1999 (EP) .............................. 99630066

(51) Int. Cl.[7] .............................. A61B 17/56

(52) U.S. Cl. .............................. 606/61; 606/60

(58) Field of Search .............................. 606/71, 60, 61, 606/73, 75, 70, 72, 74, 212; 403/400, 395; 411/459, 460, 469, 470, 920, 921

(56) References Cited

U.S. PATENT DOCUMENTS

| 1,282,848 A | * 10/1918 | Jones | 403/400 |
| 5,716,335 A | * 2/1998 | Jackson et al. | 606/61 |
| 6,027,533 A | * 2/2000 | Olerud | 606/60 |
| 6,231,575 B1 | * 5/2001 | Krag | 606/61 |
| 6,280,443 B1 | * 8/2001 | Gu et al. | 606/61 |

* cited by examiner

Primary Examiner—Pedro Philogene
(74) Attorney, Agent, or Firm—Thomas S. Baker, Jr.

(57) ABSTRACT

Flexible fastening device designed to interlock a longitudinal element (1) and an osseous anchor device (2), either internal, in particular vertebral, or external, the anchor device (2) comprising an intra-osseous part and an extra-osseous part (20) associated to a tightening device (21), the fastening device (10) comprising a first connection part (13a) and a second connection part (13b) designed to receive the extra-osseous part (20) of the anchor device (2), and an intermediate part (12a, 12b) joining the first and second connection parts (13a, 13b) and designed to encircle tightly the longitudinal element (1), the flexible fastening device (10) comprising a strand (11) out of elastic material or of material in the process of phase transformation, and the intermediate part (12a, 12b) comprising at least one spiral coil (12a, 12b) adapted to encircle the longitudinal element (1), so that a bringing closer of the first and second connection parts (13a, 13b) by the tightening device (21) or by the effect of the phase transformation of the strand (11) to memory material reduces the diameter of the spiral coil (12a, 12b) to ensure the translational and rotational blocking of the longitudinal element (1).

16 Claims, 4 Drawing Sheets

FLEXIBLE FASTENING DEVICE

BACKGROUND OF THE INVENTION

The present invention relates to a flexible fastening device for attaching a longitudinal element to an internal or external osseous anchor device.

In particular, the present invention relates to a link system in particular for a typically cylindrical fastening bar comprising an osseous anchor device consisting of an intra-osseous anchor part separated from an extra-osseous part associated to a tightening element. The present invention generally relates to a fastening device designed in particular to attach said fastening bar to the anchor element.

In common practice, the connection between an osseous anchor device and an overall longitudinally shaped piece is realised by various devices such as articulated or non-articulated clamps, clamping rings or half-rings, open or close brackets, assembly nuts provided with various tightening means.

Several known systems enable the blocking of the fastening bar with relation to the osseous anchor device, but with the bar maintained in one direction and in one fixed position with relation to the anchor device. For instance, patent FR-A-2 657 775 describes in particular a spinal bar link system with the object of linking the vertebrae comprising an osseous screw anchor with a threaded head receiving a fastening device engaging the threaded head enabling the blocking of the fastening bar between said fastening device and the cone-shaped part of a locking nut engaged on the threaded head.

U.S. Pat. No. 5,716,355 describes in particular an articulated fastening device aimed at interlocking a longitudinal element of an essentially elongated shape and an osseous anchor device, which is either internal, in particular vertebral, or external, in accordance with the preamble of Claim 1. Said fastening device comprises first and second connection parts designed to receive the extra-osseous part of the anchor device. In addition, said fastening device comprises an intermediate part joining the first and second connection parts designed to fasten the longitudinal element.

Said system enables the adjustment to a certain degree of the angle formed by the axes of the bar and of the anchor device respectively within a specified plan, but after tightening it remains in a fixed and relatively rigid position and it does not feature any flexibility via a shock absorber or spring effect.

The various known fastening devices have the following disadvantages in common:

- Absence of flexibility: no shock absorber effect, no spring effect.
- Significant loss of tightening due to curved shape of longitudinal piece.
- Embrittlement of longitudinal piece due to concentration of tightening pressure.
- Lack of adaptability to a naturally irregular osseous geometry.
- Decrease of tightening effect as distance between the anchor point and the longitudinal piece increases.

It is desirable to design a fastening device able to increase the variability of angulation of the longitudinal connecting piece with relation to the anchor device while still maintaining the fastening or blocking of the two pieces which are to be joined.

Desirable characteristics for a fastening device of this type are the variability in all directions of the relative direction of the two pieces which are to be interlocked; the possibility of obtaining a higher degree of flexibility and return movement due to a spring effect; maintaining of the fastening of the longitudinal piece even if the element is deformed, longitudinally curved or exhibits an irregular surface; adaptability to an irregular osseous geometry; maintaining of the fastening when the distance between the anchor device and the longitudinal piece increases.

Previously known devices of this type have been proven to be deficient in one respect or the other in as far as obtaining the desired characteristics by means of a simple structure which is easy to assemble and use is concerned.

SUMMARY OF THE INVENTION

One object of the present invention is to provide a flexible anchor device enabling the desired characteristics to be obtained but without the need for complicated and costly instrumentation.

A further object of the present invention is to design a flexible anchor device enabling a variation in the direction of the longitudinal fastening piece with relation to the axis of the anchor device to be obtained while improving in particular the tightening of the two pieces to be joined and hence the overall blocking.

A further object of the present invention is to provide an anchor device displaying axial, radial and rotational flexibility while enabling the translational and rotational blocking of the longitudinal element even if the element is deformed, longitudinally curved or is exhibiting an irregular surface.

In accordance with the invention, these objects and others are achieved by a new flexible fastening device displaying the characteristics of the characterising features of Claim 1.

The invention is characterised in that the flexible fastening device consists of a strand out of elastic material or a material in the process of phase transformation and in that the intermediate part of said strand comprises at least one spiral coil adapted to enclose the longitudinal element, such that the bringing closer of the first and second connection parts to the strand by means of the tightening device decreases the diameter of the spiral coil such as to ensure the translational and rotational blocking of the longitudinal element.

In general terms, the present invention, which will subsequently be described in more detail, is based upon the reduction of the internal diameter formed by a metallic strand spirally coiled with jointed turns around a typically cylindrical piece, by the relative rotation of its extremities such that it accentuates the coil initially at rest.

In theory, the developed force is proportional to the number of turns and the angular displacement of the extremities.

In practice, the friction between the longitudinal piece and the inside of the spiral coil as well as the angular displacement necessary for obtaining the fastening increase with the number of coils, which leads to a preference of their number of between 1 and 3 turns. This principle has the advantage of being tolerant towards surface or geometry irregularities, such as curving or bending exhibited by the longitudinal piece which is to be immobilised. According to the invention the fastening device exhibits axial, radial and rotational flexibility on the level of both the intermediate part and the two connection parts of the strand.

A further advantage of this aspect of the invention is that the axial, radial and rotational flexibility of the spiral coils can be selected according to the shape or size of the strand and is thus adjustable.

According to an advantageous embodiment of the invention, the metallic strand made of an elastic material or even a material in the process of phase transformation (so-called memory metal) is spirally coiled around the longitudinal element to be held, for at least one turn in one direction, a first loop or half-loop is drawn before spirally coiling in an identical, preferably symmetrically manner, in the opposite direction around the longitudinal element to be maintained.

The extremities of said strand pass on either side of the anchor device and can each end in a loop, or be advantageously joined by a sliding piece, around the extra-osseous part receiving the fastening means of the anchor device.

In order to improve the tightening of the longitudinal element while maintaining the desired overall degree of flexibility, the bringing closer by the tightening means results in an angular displacement of the first loop or half-loop towards the loops or the sliding piece, which reduces the internal diameter of the spiral coils of said flexible fastening device around the longitudinal element so as to block the latter in both a translational and rotational manner, even if said element is deformed, longitudinally curved or is exhibiting an irregular surface.

Further characteristics and advantages shall emerge from the description of several embodiments of the device according to the invention. A preferred embodiment of the present invention will be described by way of example hereinafter with reference to the figures, in which:

DESCRIPTION OF THE PREFERRED EMBODIMENTS

Figure 1:
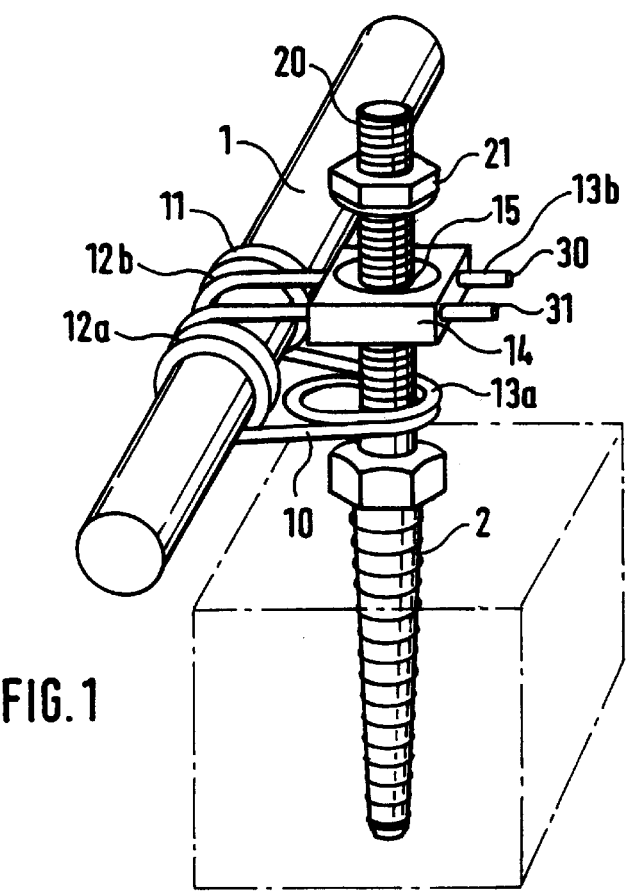
FIG. 1 is a perspective view of a device in accordance with the invention.

According to FIG. 1, the flexible fastening device aimed at interlocking a longitudinal element 1 and an osseous anchor device 2 is represented in an embodiment comprising a single metallic strand 11 out of elastic material or of material still in the process of phase transformation (memory metal), is wound in spiral coils 12*a* and 12*b* around a longitudinal element 1 in an elongated shape, generally of cylindrical revolution, with one or several flat sections, or oval and possibly exhibiting an irregular surface, according to the requirements of the application.

The strand 11 which can be circular, square or rectangular like a hoop, is formed of a biocompatible, preferably metal material and, by means of an elastic or memory effect, realises an opening position when at rest, enabling the sliding of the longitudinal piece 1.

A first spiral coil of the strand 11 is realised by at least one turn in one direction, around the longitudinal element 1, after which the strand 11 realises a first loop or half-loop 13 aimed at receiving the extra-osseous part 20 of the anchor device 2 before spiralling in a second coil 12*b* in an identical, preferably symmetrical manner, in the opposite direction around the longitudinal element 1 to be maintained.

The extremities 30 and 31 of the strand 11 pass on either side of the anchor device 2 and can each end in a loop 130 and 131 (FIG. 2), or be advantageously joined by a sliding piece 14 (FIG. 1), around the extra-osseous part 20 receiving the fastening means 21 of the anchor device 2.

The bringing closer by the fastening means 21 results in an angular displacement of the first loop or half-loop 13 towards the loops 130 and 131 or the sliding piece 14, which reduces the internal diameter of the spiral coils 12*a* and 12*b* of the flexible fastening device 10 around the longitudinal element 1 so as to tighten the latter in both a translational and rotational manner, even if said element 1 is deformed, longitudinally curved or is exhibiting an irregular surface.

According to the embodiment illustrated in FIG. 1, the sliding piece 14 is provided with an orifice 15 designed to receive the extra-osseous part 20 and can rotate by 360 degrees, swivel or move around the longitudinal axis of said extra-osseous part 20. It can in addition slide on the extremities 30 and 31 of the strand 11 so as to enable the adjustment of the distance between the longitudinal element 1 and the osseous anchor device 2. The orifice 15 designed to receive the extra-osseous part 20 is preferably shaped as a concave sphere to adapt to the spherical base of the fastening means 21 or the anchor device 2.

Figure 1A:
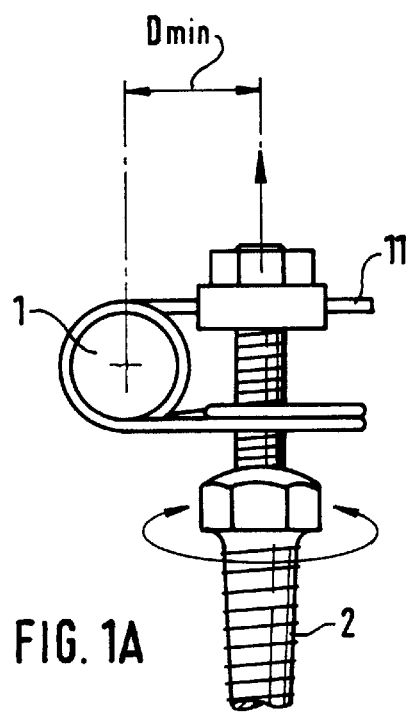
FIGS. 1A and 1B are side elevation views of the device according to FIG. 1 illustrating the possibilities of displacement around the longitudinal axis of the extra-osseous part and of sliding on the strand extremities.
Figure 1B:
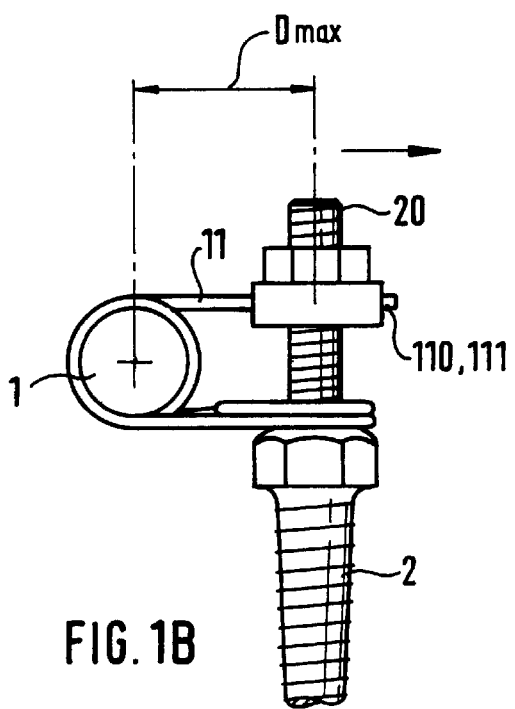

FIGS. 1A and 1B illustrate the possibilities of displacement around the longitudinal axis of the extra-osseous part 20 and of sliding on the extremities 30 and 31 of the strand 11, so as to enable an adjustment of the distance between the longitudinal element 1 and the osseous anchor device 2 via the intermediate sliding piece 14. The sliding piece 14, positioned along the extremities 30 and 31 of the strand 11 so as to enable an adjustment of the distance between the longitudinal element 1 and the osseous anchor device 2, locks into its chosen position with help of the fastening means 21.

Figure 2:
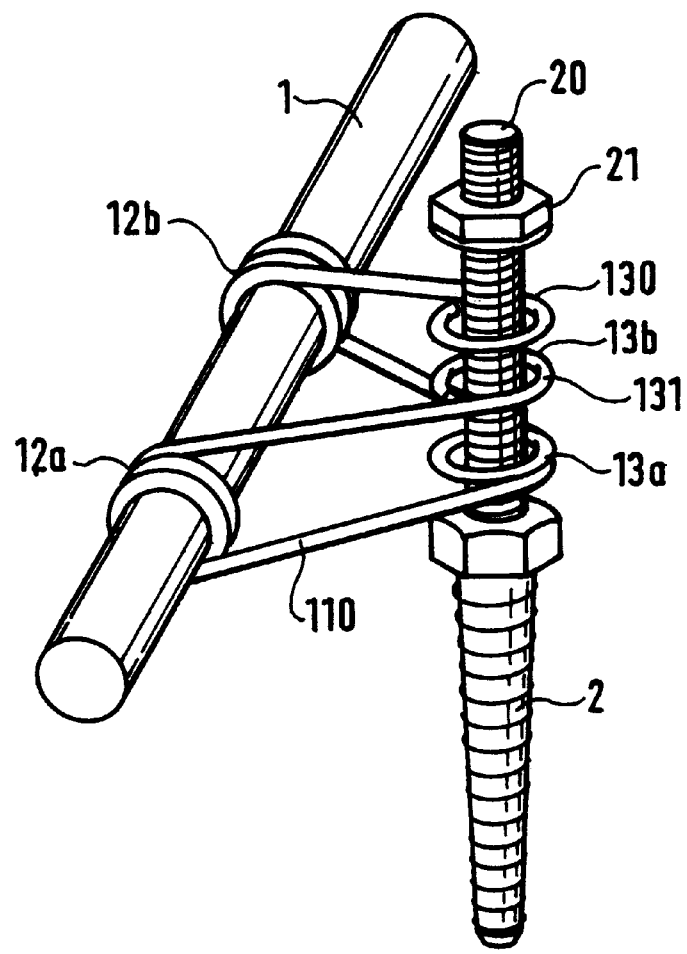
FIG. 2 is a perspective view of a further device in accordance with the invention, a variation of the device illustrated in FIG. 1.

According to the embodiment illustrated in FIG. 2, the extremities 130 and 131 of the strand 11 pass on either side of the anchor device 2 and each form a loop 130 and 131 around the extra-osseous part 20 receiving the fastening means 21 of the anchor device 2.

In a similar manner, the bringing closer by the fastening means 21 results in an angular displacement of the first loop 13*a* towards the loops 130 and 131, which reduces the internal diameter of the spiral coils 12*a* and 12*b* of the flexible fastening device 110 around the longitudinal element 1 so as to block the latter in a translational and rotational manner.

Figure 3:
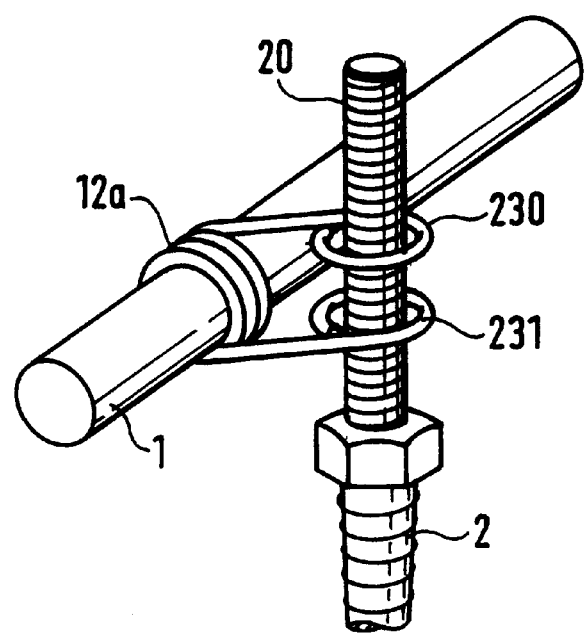
FIG. 3 is a perspective view of a further device in accordance with the invention.

FIG. 3 illustrates an embodiment of the flexible fastening device 210 comprising one single spiral coil 12*a* where the number of turns is between 1 and 5, the first extremity of which realises a first loop 230 and the second extremity a second loop 231 designed to receive the extra-osseous part 20 of the anchor device 2, around which they can pivot, swivel or slide.

This embodiment is particularly desirable for assembling a longitudinal element 1 and an osseous anchor device 2 which are not perpendicular to each other, or for creating an assembly offering a higher level of flexibility and a lower degree of alignment.

Figure 4:
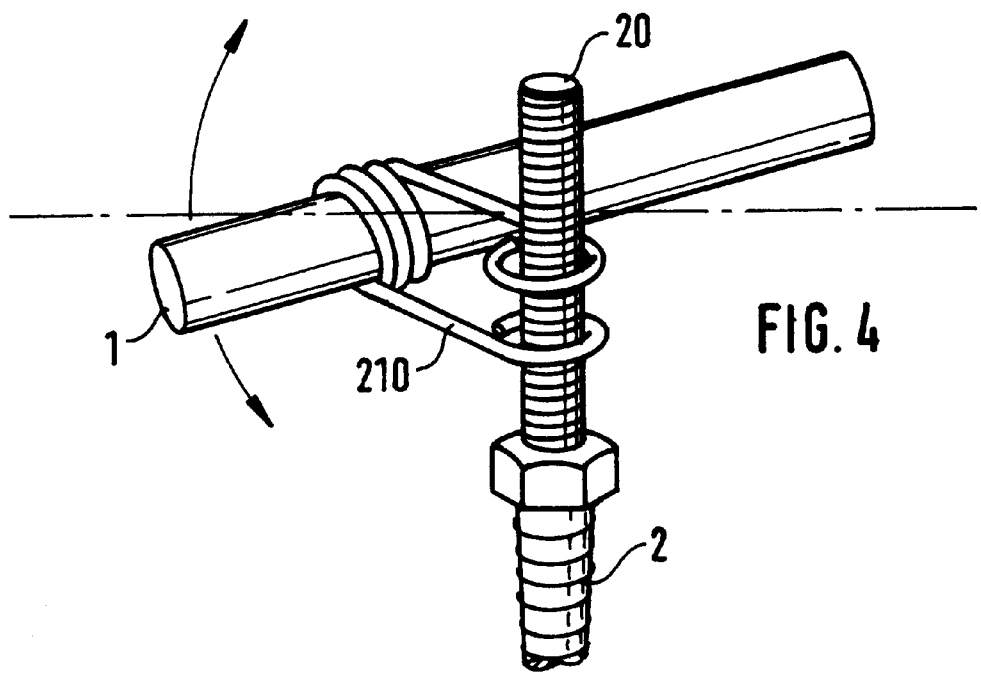
FIG. 4 is a perspective view illustrating the angular flexibility possibilities of the device according to FIG. 3.

FIG. 4 illustrates the angular flexibility possibilities enabling the assembly of a longitudinal element 1 and an osseous anchor device 2 which are not perpendicular to each other.

Figure 5:
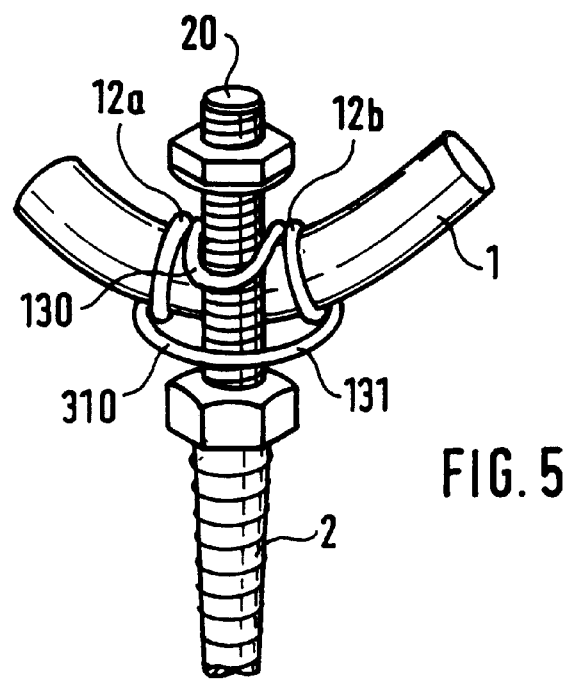
FIG. 5 is a perspective view of a further device in accordance with the invention illustrating the possibilities of axial flexibility.

According to the embodiment of FIG. 5, the spiral coil 12a of the strand 310 consists of at least one revolution in one direction, forming a first half-loop 230 designed to receive the extra-osseous part 20 of the anchor device 2, before spiralling in a second coil 12b in an identical manner, in the opposite direction around the longitudinal element 1 and forming a second half-loop 231 designed to receive the extra-osseous part 20 of the anchor device 2.

FIG. 5 illustrates the axial flexibility possibilities enabling the assembly of a longitudinal element 1 and an osseous anchor device 2, so as to block it in a translational and rotational manner, even if said element 1 is deformed, longitudinally curved or displays an irregular surface.

Figure 6:
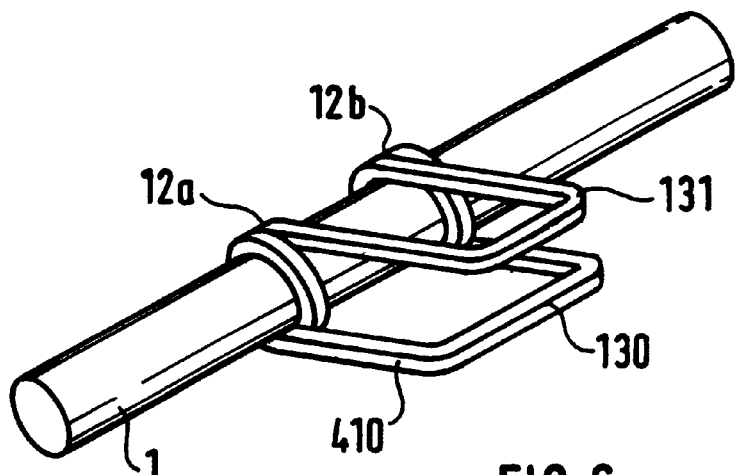
FIG. 6 is a perspective view of a further device in accordance with the invention, comprising a square strand.

FIG. 6 illustrates an embodiment of the flexible fastening device similar to that of FIG. 5, but consisting of a square strand 410.

Figure 7:
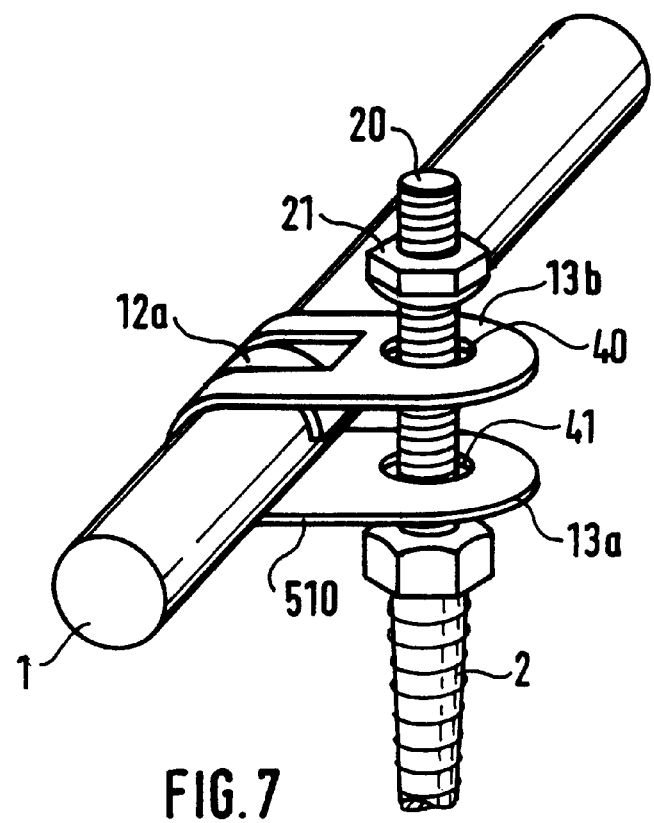
FIG. 7 is a perspective view of a further device in accordance with the invention, comprising a flat strand.

FIG. 7 illustrates an embodiment of the flexible fastening device consisting of a square strand 510. In accordance with this embodiment, the strand 510 consists of a metal strip cut so as to form a coil 12a to encircle the longitudinal element 1, and the extremities 13a and 13b of the strand 510 each comprise an orifice 40 and 41 designed to receive the extra-osseous part of the anchor device 2.

In all the above embodiments, the bringing closer by the fastening means 21 results in an angular displacement of the first and second connection parts of the strand, which reduces the internal diameter of the spiral coil(s) 12a and 12b of the flexible fastening device around the longitudinal element 1 so as to block the latter in a translational and rotational manner, even if said element 1 is deformed, longitudinally curved or is exhibiting an irregular surface.

Despite the fact that various minor adjustments can be suggested by those skilled in the art, it is obvious that other embodiments of the present invention, within the capability of those skilled in the art, could also have been conceived without stepping out of the framework of the present invention.

What is claimed is:

1. Flexible fastening device designed to interlock a longitudinal element (1) of an essentially elongated shape and an osseous anchor device (2), either internal, in particular vertebral, or external, said anchor device (2) comprising an intra-osseous part and an extra-osseous part (20) associated to a tightening means (21), said fastening device (10) comprising a first connection part (13a) and a second connection part (13b) designed to receive the extra-osseous part (20) of the anchor device (2), and an intermediate part (12a, 12b) joining said first and second connection parts (13a, 13b) and designed to encircle tightly the longitudinal element (1), characterised in that the flexible fastening device (10) comprises a strand (11) out of elastic material or of material in the process of phase transformation, and in that said intermediate part (12a, 12b) comprises at least one spiral coil (12a, 12b) adapted to encircle the longitudinal element (1), so that a bringing closer of said first and second connection parts (13a, 13b) by the tightening means (21) or by the effect of the phase transformation of the strand (11) to memory material reduces the diameter of said spiral coil (12a, 12b) to ensure the translational and rotational blocking of the longitudinal element (1).

2. Flexible fastening device according to claim 1, characterised in that the strand (11) has a circular, square or rectangular cross section, like a hoop and is formed of a biocompatible, preferably metal material and, by means of an elastic or memory effect, realises an opening position when at rest, enabling the sliding of said longitudinal piece (1).

3. Flexible fastening device according to claim 1, characterised in that said strand (11) realises a first spiral coil (12a) of at least one turn in one direction around the longitudinal element (1) to be maintained, after which it realises a loop (13a) or half-loop (13a) designed to receive the extra-osseous part (20) of the anchor device (2) before spiralling in a second, preferably symmetrical coil (12b), in the opposite direction around the longitudinal element (1) to be maintained.

4. Flexible fastening device according to claim 1, characterised in that the first and second connection parts (13a, 13b) of said strand (11) pass on either side of the anchor device (2) and each form a loop (13a, 13b) or a half-loop (230, 231) around the extra-osseous part (20) receiving the tightening means (21) of the anchor device (2).

5. Flexible fastening device according to claim 1, characterised in that it comprises in addition a sliding piece (14) and in that the extremities (30, 31) of the said strand (11) pass on either side of the anchor device (2) and are joined by said sliding piece (14) around the extra-osseous part (20) receiving the tightening means (21) of the anchor device (2).

6. Flexible fastening device according to claim 5, characterised in that the sliding piece (14) is positioned along the extremities (30, 31) of said strand (11) so as to enable an adjustment of the distance between the longitudinal element (1) and the osseons anchor device (2), before locking itself into its chosen position with help of the tightening means (21).

7. Flexible fastening device according to claim 5, characterised in that sliding piece (14) is provided with an orifice (15) designed to receive the extra-osseous part (20) and it can rotate by 360 degrees, swivel or move around the longitudinal axis of said extra-osseous part (20).

8. Flexible fastening device according to claim 7, characterised in that the orifice (15) of the sliding piece (14) designed to receive the extra-osseous part (20) is shaped as a concave sphere to enable its swing adjustment to the spherical bases of the tightening means (21) or the anchor device (2).

9. Flexible fastening device according to claim 1, characterised in that the intermediate part comprises one single spiral coil (12a) where the number of turns is between 1 and 5, and in that a first extremity of said strand realises a first loop (230) and a second extremity of said strand realises a second loop (231) designed to receive the extra-osseous part (20) of the anchor device (2), around which they can pivot, swivel or slide, to enable an assembly where the longitudinal element (1) and the osseous anchor device (2) are not perpendicular to each other, or to create an assembly offering a higher level of flexibility and a lower degree of alignment.

10. Flexible fastening device according to claim 1, characterised in that said strand consists of a metal strip (510) cut and adapted so as to coil around the longitudinal element (1)

and comprising two orifices (40, 41) designed to receive the extra-osseous part of the anchor device (2).

11. Flexible fastening device according to claim 1, characterised in that the rotational flexibility of the spiral coil(s) (12*a*, 12*b*) enables the assembly of a longitudinal element (1) and an osseous anchor device (2) which are not perpendicular to each other, or an assembly offering a higher level of flexibility and a lower level of return movement due to the spring effect of the strand (11).

12. Flexible fastening device according to claim 1; characterised in that the axial and radial flexibility of the spiral coil(s) (12*a*, 12*b*) enable the translational and rotational blocking of the longitudinal element (1) even if said element (1) is deformed, longitudinally curved or is exhibiting an irregular surface.

13. Flexible fastening device according to claim 1, characterised in that the axial, radial and rotational flexibility of the spiral coil(s) (12*a*, 12*b*) is selected according to the shape and size of the strand (11).

14. Flexible fastening device according to claim 9, characterised in that the rotational flexibility of the spiral coil(s) (12*a*, 12*b*) enables the assembly of a longitudinal element (1) and an osseous anchor device (2) which are not perpendicular to each other, or an assembly offering a higher level of flexibility and a lower level of return movement due to the spring effect of the strand (11).

15. Flexible fastening device according to claim 9, characterised in that the axial and radial flexibility of the spiral coil(s) (12*a*, 12*b*) enable the translational and rotational blocking of the longitudinal element (1) even if said element (1) is deformed, longitudinally curved or is exhibiting an irregular surface.

16. Flexible fastening device according to claim 9, characterised in that the axial, radial and rotational flexibility of the spiral coil(s) (12*a*, 12*b*) is selected according to the shape and size of the strand (11).

* * * * *